United States Patent [19]

Fujiwara et al.

[11] 4,383,037
[45] May 10, 1983

[54] PROCESS TO PRODUCE ANTHRACYCLINE GLYCOSIDES

[75] Inventors: Akiko Fujiwara; Tatsuo Hoshino, both of Kamakura; Yuzuru Sekine, Yokohama, all of Japan

[73] Assignee: Hoffmann-La Roche Inc., Nutley, N.J.

[21] Appl. No.: 313,066

[22] Filed: Oct. 19, 1981

[30] Foreign Application Priority Data

Oct. 27, 1980 [GB] United Kingdom ................ 8034536

[51] Int. Cl.³ ...................... C12P 19/56; C12R 1/465
[52] U.S. Cl. ....................................... 435/78; 435/886
[58] Field of Search ......................................... 435/78

[56] References Cited

U.S. PATENT DOCUMENTS 4,329,339  5/1982  Fujiwara et al. ..................... 435/78

OTHER PUBLICATIONS

Journal of Antibiotics, vol. 32, pp. 472–481, (May 1979).
Umezawa et al, The Journal of Antibiotics, (Japan), vol. 28, No. 10, pp. 830–835, (Oct. 1975).

Primary Examiner—Lionel M. Shapiro
Attorney, Agent, or Firm—Jon S. Saxe; Bernard S. Leon; Frank P. Hoffman

[57] ABSTRACT

There is presented a process for producing anthracycline glycosides A by converting the sugar moiety of anthracycline glycosides B, represented by the following formula:

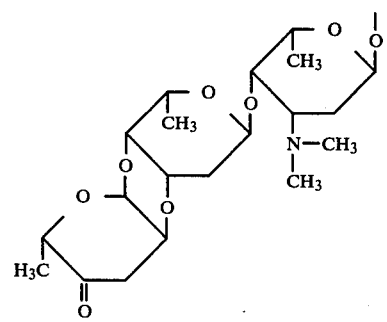

into the sugar moiety of anthracycline glycosides A, represented by the following formula:

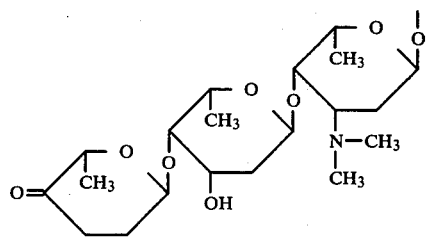

with the aid of a microorganism belonging to the species *Streptomyces galilaeus* or *Streptomyces melanogenes*.

7 Claims, No Drawings

PROCESS TO PRODUCE ANTHRACYCLINE GLYCOSIDES

DESCRIPTION OF THE INVENTION

The present invention relates to a process for the preparation of anthracycline glycosides A.

More particularly, the present invention relates to a process for producing anthracycline glycosides A by converting the sugar moiety of anthracycline glycosides B, represented by the following formula,

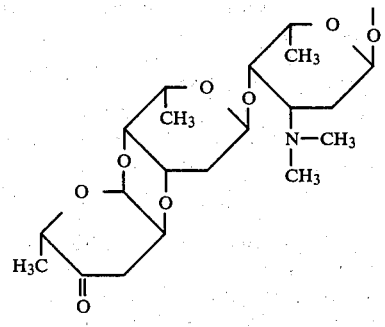

B into the sugar moiety of anthracycline glycosides A, represented by the following formula,

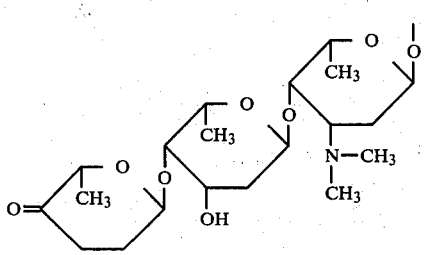

A with the aid of a microorganism belonging to the species *Streptomyces galilaeus* or *Streptomyces melanogenes*.

It is known that anthracycline glycosides A and B are effective against tumours. Furthermore, according to the article, i.e. Umezawa et al., "New antitumor antibiotics, Aclacinomycin A and B", J. Antibiotics, 28,830,1975, it is reported that the antitumor activity of aclacinomycin A is stronger than that of aclacinomycin B. However, according to the conventional fermentation method, there are obtained not only anthracycline glycosides A but also anthracyline glycosides B.

The process provided by the present invention enables anthracycline glycosides A having the stronger antitumor acitivity to be manufactured from anthracycline glycosides B in high yield and in a very simple manner. This process comprises converting the sugar moiety of anthracycline glycosides B, represented by the aforementioned formula B, into the sugar moiety of athracycline glycosides A, represented by the aforementioned formula A, with the air of a microorganism belonging to the species *Streptomyces galilaeus* or *Streptomyces melanogenes*, and capable of converting said anthracycline glycoside B into the corresponding anthracycline glycoside A.

The process provided by the present invention conveniently applies to the process for producing especially aclacinomycin A, auramycin A, sulfurmycin A, cinerbin A, 1-hydroxyauramycin A or 1-hydroxysulfurmycin A from each corresponding anthracycline glycoside B.

The chemical structures of said anthracycline glycosides A and B are as follows.

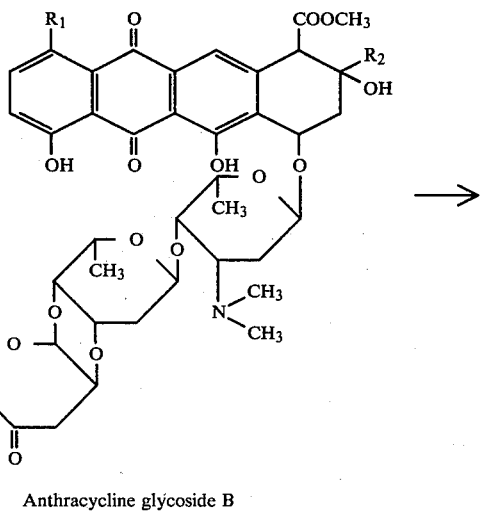

Anthracycline glycoside B

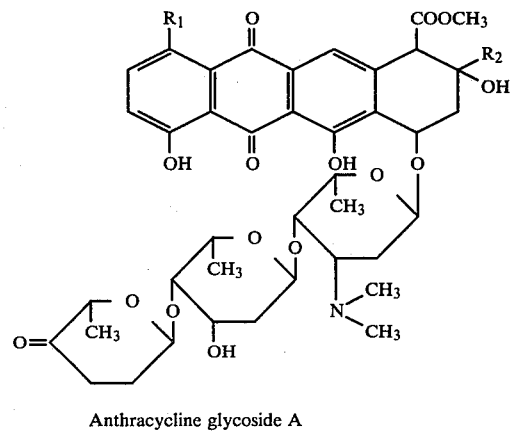

Anthracycline glycoside A

| Anthracycline glycosides | $R_1$ | $R_2$ |
|---|---|---|
| Aclacinomycin | H | $CH_2CH_3$ |
| Auramycin | H | $CH_3$ |
| Sulfurmycin | H | $CH_2COCH_3$ |
| Cinerubin | OH | $CH_2CH_3$ |
| 1-Hydroxyauramycin | OH | $CH_3$ |
| 1-Hydroxysulfurmycin | OH | $CH_2COCH_3$ |

The microorganism used in the process provided by the present invention is a microorganism belonging to the species *Streptomyces galilaeus* or *Streptomyces melanogenes* and capable of converting anthracycline glycosides B into the corresponding anthracycline glycosides A.

Preferred strains which can be used in the process provided by the present invention are *Streptomyces galilaeus* OBB-111, *Streptomyces galilaeus* OBB-731 and *Streptomyces galilaeus* FR-401 which have been isolated from soils in Neuschwanstein, Oberammergau and Murnau respectively, Oberbayern, West Germany; and *Streptomyces galilaeus* AC-628 and *Streptomyces melanogenes* AC-180 which have been isolated from soils in Ohtsu, Kumamoto-ken and Atami, Shizuoka-ken respectively, Japan; as well as mutants and variants thereof, preferably *Streptomyces galilaeus* OBB-111-848 derived from the strain *Streptomyces galilaeus* OBB-111 by treatment with N-methyl-N'-nitro-N-nitrosoguanidine. Such mutants can be obtained from the parent strains by conventional mutation methods, for example by irradiation with UV light, X-rays or γ-rays, or by treatment with suitable mutagens. The strains *Streptomyces galilaeus* OBB-111, *Streptomyces galilaeus* OBB-731, *Streptomyces galilaeus* FR-401, *Streptomyces galilaeus* AC-628, *Streptomyces melanogenes* AC-180 and *Streptomyces galilaeus* OBB-111-848 have been deposited in the Agency of Industrial Science and Technology, Fermentation Research Institute, Japan, under FERM-P No. 4780, FERM-P No. 5402, FERM-P No. 4882, FERM-P No. 4783, FERM-P No. 4782 and FERM-P No. 5316 respectively and at the American Type Culture Collection, Rockville, Md., USA under ATCC Nos. 31533, 31615, 31535, 31573, 31572, and 31598 respectively.

The mycological characteristics thereof are as follows:

1. Morphological Properties

The strain OBB-111 (FERM-P No. 4780, ATCC 31533) and the strain OBB-731 (FERM-P No. 5402; ATCC 31615) form moderately long aerial mycelium from substrate mycelium. Hooks or spirals are observed to develop at the apex of the aerial mycelium, but no whorls are formed. Mature spore chains with more than 10 spores per chain are usually produced. The spores are cylindrical, measure 0.5 to $0.6\mu \times 0.3$ to $1.0\mu$ and their surface is smooth.

The strain FR-401 (FERM-P No. 4882, ATCC 31535) forms aerial mycelium, branched like tufts, from substrate mycelium. Spirals are observed to develop, but no whorls are formed. Mature spore chains with more than 10 spores per chain are usually produced. The spores are cylindrical or ellipsoidal, mreasure 0.6 to $0.8\mu \times 0.8$ to $1.2\mu$ and their surface is smooth.

The strain AC-628 (FERM-P No. 4783; ATCC 31573) developed abundantly aerial mycelia from substrate mycelia. The aerial mycelia formed spirals, but whorl formation was not recognized. Mature spore chain was generally more than 10 spores per chain. The spore was of $0.6 \sim 1.0\mu 1.0 \times 1.4\mu$ in diameter, cylindrical in shape and its surface was smooth.

The strain AC-180 (FERM-P No. 4782; ATCC 31572) only poorly developed aerial mycelia from substrate mycelia. The aerial mycelia formed were straight to flexuous. Neither spiral nor whorl formation was observed. Mature spore chain was generally more than 10 spores per chain. The spore was of $0.4 \sim 0.6 \times 0.8 \sim 1.2\mu$ in diameter, cylindrical in shape and its surface was smooth.

2. Culture Characteristics on Various Media

The culture characteristics of strains OBB-111, OBB-731, FR-401, AC-628 and AC-180 are shown in Table 1.

3. Physiological Characteristics

The physiological characteristics and carbohydrate utilization of the strains OBB-111, OBB-731, FR-401, AC-628 and AC-180 are shown in Table 2 and Table 3, respectively.

TABLE 1.

| Medium | Strain OBB-111 | Strain FR-401 | Strain AC-628 | Strain OBB-731 | Strain AC-180 |
|---|---|---|---|---|---|
| Sucrose-nitrate agar | | | | | |
| Growth | dull orange [4pe, Orange Rust] | brown [6ni, Taupe Brown]~pale reddish orange [6ie, Redwood] | colorless~ pale orange | pale yellow~pale yellowish brown [3gc, Light Tan] | pink [6gc, Dusty Coral]~dull purple [9le, Raspberry] |
| Aerial Mycelium | brownish gray [3cb, Sand]~pale orange [5cb] | pinkish white [6ge, Rose Gray] | light gray [2fe, Covert Gray] | brownish gray [3cb, Sand]~pale orange [5cb] | none |
| Diffusible Pigment | reddish | reddish | none | yellowish | reddish |
| Glucose-asparagine agar | | | | | |
| Growth | dull orange [3pe, Topaz~3ne, Topaz] | pale orange [4ge, Rose Beige] | yellowish gray [2ec, Oatmeal] | dull orange [3pe, Topaz~3ne, Topaz] | brownish gray [3li, Beaver]~dark yellowish brown [3pn, Cepla Brown] |
| Aerial Mycelium | light brownish gray [3dc, Natural] | none | none | light brownish gray [3dc, Natural] | none |
| Diffusible Pigment | brownish | brownish | none | brownish | brownish |
| Glycerol-asparagine agar | | | | | |
| Growth | pale yellow~pale yellowish brown [3gc, Light Tan~3lc, Amber] | dull reddish orange [5le, Rust Tan~5ne Tile Red] | light reddish orange [5pa, Brite Orange] dull reddish orange [5ne, Tile Red] | pale yellow [3gc, Light Tan]~pale yellowish brown [3lc, Amber] | grayish red [7pi, Dark Wine]~dark brownish purple [7pn, Dark Rose Brown] |
| Aerial Mycelium | light gray [2fe, Covert Gray] | light gray [2fe, Covert Gray] | light gray [2fe, Covert Gray~3fe, Silver Gray] | light gray [2fe, Covert Gray] | pale pink [7cb, Cloud Pink~7ec, Rose Mist] |
| Diffusible Pigment | none | brown | reddish | yellow | brownish |
| Starch-inorganic salts agar (ISP medium No. 4) | | | | | |
| Growth | pale yellow [2pc, Brite Gold]~dull yellow | grayish yellow [3ec, Bisque]~pale | yellowish gray [2ec, Oatmeal] | pale yellow [2pc, Brite Gold]~dull yellow | light brown [4ng, Light Brown]~dark brown |

TABLE 1.-continued

| | Culture characteristics on various media | | | | |
|---|---|---|---|---|---|
| Medium | Strain OBB-111 | Strain FR-401 | Strain AC-628 | Strain OBB-731 | Strain AC-180 |
| | [2pe, Mustard Gold] | yellowish brown [3ge, Lt Tan] | ~light reddish orange [5pa, Brite Orange] | [2pe, Mustard Gold] | [4pn, Dark Brown] |
| Aerial Mycelium | light brownish gray [2dc, Natural]~light gray [2fe, Covert Gray] | light brownish gray [3dc, Natural] | light gray [3fe, Covert Gray] | light brownish gray [2dc, Natural]~light gray [2fe, Covert Gray] | pale pink [7ba, Pink Tint]~pink [7ca, Pale Pink] |
| Diffusible Pigment | yellow | brownish | brownish | yellow | brown |
| Tyrosine agar (ISP medium No. 7) | | | | | |
| Growth | dark brownish gray [3ni, Clove Brown] | brownish violet [4pe, DK Spice Brown] | brown [5ni, Cocoa Brown] ~dull reddish orange [5le, Rust Tan] | dark brownish gray [3ni, Clove Brown] | brown [5ni, Cocoa Brown]~dark brown [5nl, Dark Brown] |
| Aerial Mycelium | none | light gray [3fe, Silver Gray] | light gray [3fe, Covert Gray]~light brownish gray [5fe, Ashes] | none | pale pink [7ba, Pink Tint] |
| Diffusible Pigment | black | brown | brown | black | dark brown |
| Nutrient agar | | | | | |
| Growth | colorless~pale brown | colorless~pale brown | pale brown [3ie, Camel] | colorless~pale brown | pale brown [4ge, Light Fawn] |
| Aerial Mycelium | none | none | none | none | none |
| Diffusible Pigment | none | none | none | brown | none |
| Yeast extract-malt extract agar (ISP medium No. 2) | | | | | |
| Growth | yellowish brown [3ng, Yellow Maple] | pale yellowish brown [3ie, Camel] | dull red [5ie, Copper Tan]~reddish brown [5ng, Brick Red] | yellowish brown [3ng, Yellow Maple] | dull red [7ng, Old Wine] ~dark brownish purple [8pl, Cordvan] |
| Aerial Mycelium | light gray [2fe, Covert Gray] | light gray [2fe, Covert Gray]~light brownish gray [3dc, Natural] | light brownish gray [5fe, Ashes~7fe, Ashes] | light gray [2fe, Covert Gray] | brownish gray [3cb, Sand] |
| Diffusible Pigment | none | none | brownish | none | brown |
| Oatmeal agar (ISP medium No. 3) | | | | | |
| Growth | pale yellowish brown [2gc, Bamboo]~pale brown [3ie, Camel] | pale yellowish brown [3ie, Camel] ~pale reddish brown [4ge, Nude Tan] | pale brown [4gc, Nude Tan] ~reddish brown [6ng, Brick Red] | pale yellowish brown [2gc, Bamboo]~pale brown [3ie, Camel] | dark red [6pi, Brown Mahogany]~dark brownish purple [6pn, Dark Brown Mahogany] |
| Aerial Mycelium | light gray [2fe, Covert Gray~3fe, Silver Gray] | light grayish reddish brown [5fe, Ashes] | light gray [2fe, Covert Gray]~dark gray [3ih, Beige Gray] | light gray [2fe, Covert Gray~3fe, Silver Gray] | none |
| Diffusible Pigment | brown | red | reddish | brown | reddish |
| Skimmed milk (37° C.) | | | | | |
| Growth | brown~dark brown | brown~dark brown | pale brown ~brown | brown~dark brown | colorless~pale brown |
| Aerial Mycelium | white~brownish gray | none | none | white~brownish gray | none |
| Diffusible Pigment | dark brown | dark brown | dark brown | dark brown | none |
| Glucose peptone gelatin stab | | | | | |
| Growth | pale yellow | colorless | colorless~pale yellowish brown | pale yellow | colorless~pale yellowish brown |
| Aerial Mycelium | none | none | yellowish gray | none | none |
| Diffusible Pigment | brown | brown | brown | brown | faint brownish |

TABLE 2.

Physiological characteristics of the 5 strains

| Test | OBB-111, OBB-731 FR-401 and AC-6288 | AC-180 | Methods and Materials Used |
|---|---|---|---|
| Gelatin liquefaction | moderate liquefaction | weak liquefaction | glucose-peptone-gelatin medium: 27° C. |
| Starch hydrolysis | weak to moderate hydrolysis | moderate hydrolysis | starch-inorganic salts agar |
| Peptonisation and coagulation of skimmed milk | moderate to strong peptonisation and no coagulation | strong coagulation and weak peptonization | 10% skimmed milk; 37° C. |
| Nitrate reduction | positive | negative | ISP medium No. 8; 27° C. |
| Melanin formation | positive | positive | ISP medium No. 1 ISP medium No. 6 ISP medium No. 7 |

TABLE 3.

Carbohydrate utilization

| | OBB-111, OBB-731 FR-401 and AC-6288 | AC-180 |
|---|---|---|
| L-Arabinose | positive | positive |
| D-Xylose | positive | positive |
| Glucose | positive | positive |
| D-Fructose | positive | positive |
| Sucrose | positive | positive |
| Inositol | positive | positive |
| L-Rhamnose | positive | positive |
| Raffinose | positive | positive |
| D-Mannitol | negative | positive |

Basal medium: Pridham-Gottlieb medium (ISP medium No. 9)
Temperature: 27° C.

The foregoing characteristics of strains OBB-111, OBB-731, AC-628 and FR-401 can be summarised as follows: The strains belong to the genus Streptomyces. The aerial mycelium forms spirals at the apex but no whorls. The surface of the spores is smooth. The growth on various media is found to be pale yellowish brown to pale brown or dull orange, and the aerial mycelium is light grey. The strains produce reddish to brown diffusible pigment and melanin on various media. Among known species of Streptomyces, strains OBB-111, OBB-731, AC-628 and FR-401 resemble *Streptomyces galilaeus* (Reference 1: Archiv für Mikrobiologie, 31, 356, 1958. Reference 2: The Actinomycetes, 2, 215, 1961. Reference 3: International Journal of Systematic Bacteriology, 22, 298, 1972) and *Streptomyces galilaeus* MA 144-M1, FERM-P No. 2455 (Reference 1: Japanese Patent Publication No. 34915/1976). The differences between the present strains and the standard strains of *S. galilaeus* ISP 5481 and *S. galilaeus* MA 144-M1 (FERM-P No. 2455) were investigated by parallel cultures. The results are shown in Table 4 hereinafter.

TABLE 4

| | OBB-111, OBB-731, FR-401 and AC-628 | S. galilaeus ISP 5481 | S. galilaeus MA 144-M1 (FERM-P No. 2455) |
|---|---|---|---|
| Liquefaction of gelatin | moderate | weak to moderate | weak to moderate |
| Coagulation of milk | negative | weak positive | negative |
| Diffusible pigment | dark brown | light brown | dark brown |
| Change of colour of growth by 0.05N sodium hydroxide solution: | | | |
| ISP medium No. 3 | pink to violet | — | pink to violet |
| ISP medium No. 4 | slight pink ~violet | — | slight pink ~violet |
| ISP medium No. 5 | violet | slight violet | violet |

From the results, the present strains are very similar to *S. galilaeus* ISP 5481 and *S. galilaeus* MA 144-M1 (FERM-P No. 2455) in morphology and colour of the growth and mycelium on various media, chromogenicity and utilization of carbohydrates, although some differences were observed. We, therefore, concluded that OBB-111 (FERM-P No. 4780), OBB-731 (FERM-P No. 5402), FR-401 (FERM-P No. 4782) and AC-628 (FERM-P No. 4783) belong to a species of *Streptomyces galilaeus* and named *Streptomyces galilaeus* OBB-111, OBB-731, FR-401 and AC-628, respectively.

On the other hand, strain AC-180 (FERM-P No. 4782), belonging to genus Streptomyces, developed straight to flexuous aerial mycelia, though poorly. The spore surface was smooth. Growth was dark brown to dark brownish purple and developed poorly aerial mycelia of pale pink on ISP Medium 2, 4, 5 and 7, however no aerial mycelium was formed on sucrose nitrate agar, glucose asparagine agar, nutrient agar and ISP Medium 3. Reddish to brownish pigment was produced in various agar media. Melanoid pigment was produced in ISP-Medium 1, 6 and 7. In carbon utilization test, abundant growth was seen with L-arabinose, D-xylose, glucose, D-fructose, inositol, L-rhamnose, raffinose and D-mannitol. Sucrose seemed probably utilized. With skimmed milk test, both coagulation and peptonization were observed. Starch hydrolysis and gelatin liquefaction were positive, while nitrate was not reduced to nitrite.

When all the above properties were compared with known species of Streptomyces, it was found that many features of AC-180 (FERM-P No. 4782) were common with strain *Streptomyces malanogenes* (Int. J. Syst. Bact., 18, p. 348, 1968; J. Antibiot., Tokyo Ser. A, 10, 138~142, 1957). Thus a comparative study was undertaken with *Streptomyces melanogenes* IFO 12890 by parallel culture, the results of which are summarized in Table 5. The strain AC-180 (FERM-P No. 4782) differed from *Streptomyces melanogenes* IFO 12890 strain in L-rhamnose utilization and the color of reverse side (AC-180 (FERM-P No. 4782) was purplish color strong) on ISP-Medium 5. However, these differences were small in balance with other great similarities in morphology cultural and physiological properties. Thus, we concluded that strain AC-180 (FERM-P No. 4782) should be reasonably a species of *Streptomyces melanogenes* and identified *Streptomyces melanogenes* AC-180.

TABLE 5.

Comparison of strain AC-180 with *Streptomyces melanogenes* IFO 12890

| | AC-180 (FERM-P No. 4782) | St. melanogenes IFO 12890 |
|---|---|---|
| Morphology of aerial mycelium | straight to flexuous | straight to flexuous |
| Color of aerial mycelium | red to gray color series | red to gray color series |
| Condition of aerial mycelium | none or scant | moderate |
| Reverse side color (on ISP-Medium 5) | dark brown to dark brownish purple | brown to dark brown |
| Soluble pigment | reddish to brownish | brownish |
| Skimmed milk | | |
| Coagulation | + | + |
| Peptonization | + | + |
| Gelatin liquefaction | + | + |
| Nitrate reduction | − | − |
| Carbon utilization | | |
| L-arabinose | ++ | ++ |
| D-xylose | ++ | ++ |
| Glucose | ++ | ++ |
| D-fructose | ++ | ++ |
| Sucrose | + | + |
| Inositol | ++ | ++ |
| L-rhamnose | ++ | − |
| Raffinose | ++ | ++ |
| D-mannitol | ++ | ++ |

*Streptomyces galilaeus* OBB-111-848 (FERM-P No. 5316; ATCC 31598) is the strain derived from *Streptomyces galilaeus* OBB-111 (FERM-P No. 4780, ATCC 31533) by the following method.

The spores of an agar slant culture of *Streptomyces galilaeus* OBB-111 (FERM-P No. 4780, ATCC 31533) were suspended in 10 ml of sterile physiological saline solution and filtered through a glass filter No. 3. The spores were resuspended and diluted 2-fold with 0.2 M tris buffer (pH 9.0) containing 2 mg/ml of N-methyl-N'-nitro-N-nitrosoguanidine and incubated at 27° C. for 60 minutes. Then the spores were collected on the Nucleopore filter (0.2 μm pore size), washed with 30 ml of sterile physiological saline solution and resuspended in 10 ml of sterile physiological saline solution. The spore suspension thus obtained was spread on the ISP-No. 2 medium in a Petri dish and incubated at 27° C. for 4~6 days. The colonies were picked up and transferred to an agar slant and incubated for 10~14 days. The strains thus obtained were tested for production of auramycinone and sulfurmycinone glycosides according to the following procedure.

The spores of each strain was inoculated into 10 ml of the medium in a test tube consisting of 2% glucose, 2% soluble starch 1% Pharmadmeia (Traders Oil Mill Co., U.S.A.), 0.1% $K_2HPO_4$, 0.1% $MgSO_4.7H_2O$, 0.3% NaCl and 0.3% $CaCO_3$ and cultured for 4 days at 27° C. on a reciprocal shaker. The culture broth was extracted with 20 ml of a solvent mixture of chloroform and methanol (1:1, v/v) and chloroform layer recovered. After concentration to dryness, the extract was dissolved in 0.5 ml of chloroform and analyzed on silica gel tlc plates developed with toluene/methanol (10:1).

*Streptomyces galilaeus* OBB-111-848 (FERM-P No. 5316; ATCC 31598) was selected as a non-producer of anthracycline pigments.

The microorganism can be used in a form of the culture broth, mycelia or enzyme. The culture broth can be prepared by inoculating a suitable medium with the microorganism. The culture medium can contain carbon sources, nitrogen sources, inorganic salts and other nutrient substances suitable for the growth of the microorganisms. Preferred carbon sources are glucose, sucrose, dextrin, mannose, starch, lactose, glycerol and the like. The nitrogen sources are, for example, nitrogen-containing organic substances such as peptone, meat extract, yeast extract, corn steep liquor, casein and the like, or nitrogen-containing inorganic compounds such as nitrates and inorganic ammonium salts. Examples of inorganic salts are phosphates or sodium, potassium, manganese, magnesium, iron copper salts and the like.

The cultivation of the microorganism may be carried out as a submerged culture, as a shaking culture or as a stationary culture. In a preferred embodiment, the microorganism is cultured under aerobic conditions.

The process provided by the present invention is conveniently carried out by adding an anthracycline glycoside B to the cultivated culture broth. The concentration of the anthracycline glycoside B conveniently is up to 1 g/l. The corresponding anthracycline glycoside A can be obtained by continuing the incubation of the microorganism under the aforementioned conditions. The incubation time can vary depending on the microorganism used, on the composition of the culture medium, on the anthracycline glycoside B used and on its concentration. However, in general, an incubation time of several hours suffices. The cultivation temperature generally lies between 20° C. and 30° C. Furthermore, the cultivation is conveniently carried out at a pH of 5 to 7.

The anthracycline glycisode B can be added to the culture of the microorganism during the cultivation or to the culture medium prior to sterilization or inoculation.

The transformation product can be isolated from the fermentation mixture in a manner known per se; for example, by solvent extraction with an organic solvent such as chloroform, methanol, and the like, and/or by chromatography on a carrier such as silica gel, aluminium oxide and the like. The product can be also purified by recrystalization from an organic solvent.

According to another aspect of preferred embodiment of the process provided by the present invention, the reaction can be carried out in the presence of the mycelium isolated from the culture broth of the microorganism or an enzyme extract prepared in a manner known per se from the culture broth or the mycelium, in a solution, for example, a buffer solution, in physiological salt solution, in fresh nutrient solution or in water.

The following Examples illustrate the present invention:

EXAMPLE 1

100 ml of sterilized medium in a 500 ml Erlenmeyer flask were inoculated with a slant of *Streptomyces galilaeus* OBB-111-848 (FERM-P No. 5316, ATCC 31598). The composition of said medium is as follows: glucose 2%, soluble starch 2%, Pharma Media (Traders Oil Mill Co., U.S.A.) 1% $K_2HPO_4$ 0.1%, $MgSO_4.7H_2O$ 0.1%, NaCl 0.3% and $CaCO_3$ 0.3%. The flask was incubated at 27° C. for 3 days on a rotary shaker operating at 180 rpm.

2 ml of the culture thus obtained were seeded into each of three 500 ml flasks containing 100 ml of medium with the same composition as mentioned above. After cultivation at 27° C. for 3 days, to each flask were added 5 mg of aclacinomycin B, auramycin B or sulfurmycin B dissolved in 2 ml of methanol and the flasks were further incubated. After 1, 3 and 7 hours, 5 ml aliquots were removed from each flask and extracted with chloroform/methanol (1:1, v/v); and the extract was analyzed on thin layer chromatographic plates developed with a solvent mixture of toluene and methanol (10:1, v/v).

The results are shown in Table 6

TABLE 6

| Reaction time | Products {(A/A + B) × 100} | | |
|---|---|---|---|
| | Aclacinomycin A | Auramycin A | Sulfurmycin A |
| 1 hr. | 22.5% | 20.4% | 23.3% |
| 3 hr. | 47.8 | 40.7 | 40.0 |
| 7 hr. | 63.2 | 75.0 | 81.3 |

EXAMPLE 2

100 ml of sterilized medium in a 500 ml Erlenmeyer flask were inoculated with a slant culture of *Streptomyces galilaeus* OBB-111-848 (FERM-P No. 5316, ATCC 31598). The composition of said medium is as follows: glucose 2%, soluble starch 2%, Pharma Media (Traders Oil Mill Co., U.S.A.) 1%, $K_2HPO_4$ 0.1%, $MgSO_4.7H_2O$ 0.1%, NaCl 0.3% and $CaCO_3$ 0.3%. The flask was incubated at 27° C. for 3 days on a rotary shaker operating at 180 rpm.

5 ml of the culture thus obtained were transferred into each of three 500 ml flasks containing 100 ml of medium with the same composition as mentioned above. After cultivation at 27° C. for 2 days, the cells were collected by centrifugation and distributed into three 500 ml flasks containing 5 mg of aclacinomycin B, auramycin B or sulfurmycin B in 100 ml of sterilized saline solution. The flasks were incubated at 27° C. on a rotary shaker.

After 1, 3 and 7 hours, 5 ml aliquots were removed and extracted with chloroform/methanol (1:1, v/v); and the extract was analyzed by high pressure liquid chromatography.

The results thereof are shown in Table 7.

TABLE 7

| Reaction time | Products (A/A + B) × 100 | | |
|---|---|---|---|
| | Aclacinomycin A | Auramycin A | Sulfurmycin A |
| 1 hr. | 35.5% | 38.2% | 41.7% |
| 3 hr. | 48.8 | 52.9 | 55.8 |
| 7 hr. | 58.8 | 65.0 | 68.2 |

EXAMPLE 3

In a manner analogous to that described in Example 2, using cinerubin B, 1-hydroxyauramycin B and 1-hydroxysulfurmycin B respectively, there were obtained the conversion ratios of 40%, 43% and 45%, respectively.

EXAMPLE 4

In a manner analogous to that described in Example 2, using *Streptomyces galilaeus* FR-401 (FERM-P No.4882; ATCC 31535) instead of the strain OBB-111-848, the conversion ratio of aclacinomycin B into aclacinomycin A was 79% after 5 hours.

EXAMPLE 5

In a manner analogous to that described in Example 2, using *Streptomyces galilaeus* AC-628 (FERM-P No. 4783; ATCC 31573) and *Streptomyces melanogenes* AC-180 (FERM-P No. 4782, ATCC 31572) respectively, instead of the strain OBB-111-848, the conversion ratios of cinerubin B into cinerubin A after 5 hours were 10% and 30%, respectively.

EXAMPLE 6

In a manner analogous to that described in Example 2, using *Streptomyces galilaeus* OBB-111 (FERM-P No. 4780, ATCC 31533) instead of *Streptomyces galilaeus* OBB-111-848, the conversion ratios of aclacinomycin B, auramycin B and sulfurmycin B into aclacinomycin A, auramycin A and sulfurmycin A after 7 hours were 64%, 69% and 73%, respectively.

EXAMPLE 7

The slant culture of *Streptomyces galilaeus* OBB-111-848 (FERM-P No. 5316, ATCC 31598) was inoculated into 100 ml of medium containing glucose 2%, soluble starch 2%, Pharma Media (Traders Oil Co., U.S.A.) 1%, $K_2HPO_4$ 0.1%, $MgSO_4.7H_2O$ 0.1%, NaCl 0.3%, and $CaCO_3$ 0.3% in a 500 ml Erlenmeyer flask and cultivated at 27° C. for 3 days on a rotary shaker operating at 180 rpm. 5 ml of the culture thus obtained were transferred into each of fifteen 500 ml Erlenmeyer flasks containing 100 ml of medium with the same composition as mentioned above and incubated for further 2 days under the same condition.

The culture was centrifuged at 8,000 rpm to harvest the cells. The cells were distributed into fifteen flasks containing 100 ml of sterilized saline solution with 5 mg of sulfurmycin B. The flasks were incubated at 27° C. on a rotary shaker at 180 rpm for 7 hours.

The reaction mixture was centrifuged at 8,000 rpm for 10 minutes to separate the cells from the supernatant. The cells were extracted with 1 l of the solvent mixture of chloroform and methanol (1:1, v/v), to which 500 ml of water were added to separate chloroform layer. On the other hand, the supernatant was extracted with the equal volume of chloroform. The extracts were combined and evaporated to dryness and dissolved in toluene, to which was added silica gel. The suspension was shaken overnight at room temperature.

The silica gel was collected by filtration and extracted with chloroform/methanol (5:1, v/v). The extract was evaporated to dryness under reduced pressure and dissolved in a small amount of chloroform. The purification was performed by thin layer chromatography on silica gel 60, $F_{254}$ (Merck Co.) with the solvent system toluene/methanol (10:1), whereby 39 mg of sulfurmycin A were obtained as yellow powder.

EXAMPLE 8

In a manner analogous to that described in Example 7, using auramycin B instead of sulfurmycin B, there were obtained 39 mg of auramycin A as yellow powder.

EXAMPLE 9

In a manner analogous to that described in Example 7, using *Streptomyces galilaeus* OBB-111-848 and aclacinomycin B instead of sulfurmycin B, there was obtained 50 mg of aclacinomycin A.

What is claimed:

1. A process for producing anthracycline glycosides A which comprises converting the sugar moiety of anthracycline glycosides B of the formula:

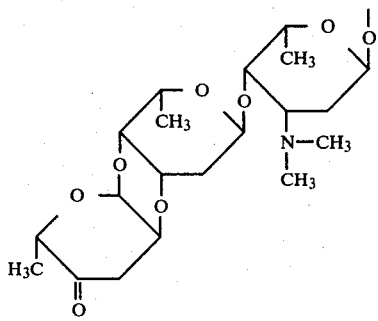

into the sugar moiety of anthracycline glycosides of the formula:

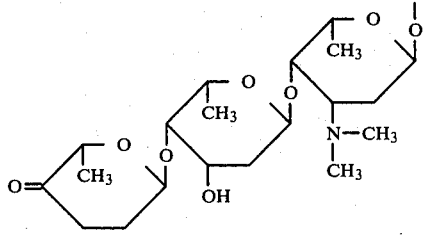

by fermentative reaction with a microorganism of the species *Streptomyces galilaeus* or *Streptomyces melanogenes*.

2. The process of claim 1, wherein the microorganism is selected from the group consisting of *Streptomyces galilaeus* OBB-111 (FERM-P No. 4780; ATCC 31533), *Streptomyces galilaeus* OBB-731 (FERM-P No. 5402; ATCC 31615), *Streptomyces galilaeus* FR-401 (FERM-P No. 4882; ATCC 31535), *Streptomyces galilaeus* AC-628 (FERM-P No. 4783; ATCC 31573), *Streptomyces melanogenes* AC-180 (FERM-P No. 4782; ATCC 31572) and *Streptomyces galilaeus* OBB-111-848 (FERM-P No. 5316; ATCC 31598).

3. The process of claim 1, wherein the anthracycline glycoside B is selected from the group consisting of aclacinomycin B, auramycin B, sulfurmycin B, cinerubin B, 1-hydroxyauramycin B or 1-hydroxysulfurmycin B.

4. The process of claim 1, wherein the anthracycline glycoside A is selected from the group consisting of aclacinomycin A, auramycin A, sulfurmycin A, cinerubin A, 1-hydroxyauramycin A or 1-hydroxysulfurmycin A.

5. The process of claim 1, wherein the anthracycline glycosides B are fermented in a culture medium and the corresponding anthracycline glycosides A are recovered from the fermentation broth.

6. The process of claim 5, wherein the substrate concentration is up to 1 g/l.

7. The process of claim 1 wherein the reaction is carried out in the presence of the mycelium isolated from the culture broth of the microorganism in a solution.

* * * * *